(12) United States Patent
Bellnier et al.

(10) Patent No.: US 6,495,585 B2
(45) Date of Patent: Dec. 17, 2002

(54) METHOD FOR TREATING HYPERPROLIFERATIVE TISSUE IN A MAMMAL

(75) Inventors: David A. Bellnier, Buffalo, NY (US); Thomas J. Dougherty, Grand Island, NY (US)

(73) Assignee: Health Research, Inc., Buffalo, NY (US)

( * ) Notice: Subject to any disclaimer, the term of this patent is extended or adjusted under 35 U.S.C. 154(b) by 34 days.

(21) Appl. No.: 09/801,163

(22) Filed: Mar. 7, 2001

(65) Prior Publication Data

US 2002/0128303 A1 Sep. 12, 2002

(51) Int. Cl.⁷ .................. A61K 31/40; A61K 31/35
(52) U.S. Cl. .................... 514/410; 514/455
(58) Field of Search .................. 514/410, 455

(56) References Cited

U.S. PATENT DOCUMENTS 4,866,168 A  *  9/1989  Dougherty et al. ......... 540/145
5,002,962 A  *  3/1991  Pandey et al. ............. 514/410

OTHER PUBLICATIONS

Mahadevan, V. et al., "Role of Tumor Necrosis Factor in Flavone Acetic Acid–Induced Tumor Vasculature Shutdown", Cancer Research 50, pp. 5537–5542, Sep. 1, 1990.*

* cited by examiner

*Primary Examiner*—Dwayne C. Jones
(74) *Attorney, Agent, or Firm*—Michael L. Dunn

(57) ABSTRACT

A novel method for treating undesired hyperproliferative tissue in a mammal. The method includes the steps of: injecting the mammal with a photodynamic compound having a selective uptake in the hyperproliferative tissue and which is activated at a particular light frequency; injecting the mammal with a xanthenone-4-acetic acid or a Group I metal, Group II metal or quaternary salt thereof near the time of maximum uptake of the photodynamic compound in the hyperproliferative tissue; and exposing the hyperproliferative tissue to light at the particular frequency that activates the photodynamic compound. The method of the invention causes necrosis of the hyperproliferative tissue to an extent greater than can be obtained by either the photodynamic compound or xanthenone-4-acetic acid alone. Further and surprisingly the method enhances immune response of the mammal to the hyperproliferative tissue even after the photodynamic compound and xanthenone-4-acetic acid are no longer present in the mammal.

7 Claims, 6 Drawing Sheets

METHOD FOR TREATING HYPERPROLIFERATIVE TISSUE IN A MAMMAL

This invention was made with support by Grant Number CA 55791 from The National Cancer Institute. The U.S. Government may have certain rights in this invention.

BACKGROUND OF THE INVENTION

This invention relates to a method for treatment of hyperproliferative tissues, such as tumors and hyperproliferative blood vessels, e.g. those associated with age related macular degeneration (AMD), using photodynamic methods. Certain photodynamic compounds, e.g. porphyrin related compounds such as derivatives of chlorins, bacteriochlorins and hematoporphyrins such as porfimer sodium compounds, when stable, may be used for that purpose. These compounds have the ability to preferentially collect in hyperproliferative tissues when injected into an organism and to absorb light to cause reduction in growth of the tissue, such as by its destruction. Such reduction in growth of hyperproliferative tissue using photodynamic compounds is collectively referred to herein as photodynamic therapy.

Photodynamic therapy (PDT) is a relatively new modality for the treatment of various types of solid tumors. Many porphyrins and related photosensitive compounds demonstrate the ability to selectively accumulate in neoplastic tissue after intravenous injection and sensitize the tissue to photoirradiation. Activation of the photosensitive agent by visible light, delivered by a laser through fiber optics, results in the generation of cytotoxic agents. It is currently accepted that the production of singlet oxygen, formed from molecular oxygen, formed from molecular oxygen by the transfer of energy directly or indirectly from the activated photosensitizer, is responsible for tumor homeostasis and the observed tumor destruction.

Following absorption of light, the photosensitizer is transformed from its ground singlet state (P) into an electronically excited triplet state ($^3P^*$; $\tau\sim 10^{-2}$ sec.) via a short-lived excited singlet state ($^1P^*$; $\tau\sim 10^{-6}$ sec.) The excited triplet can undergo non-radiative decay or participate in an electron transfer process with biological substrates to form radicals and radical ions, which can produce singlet oxygen and superoxide ($O_2^-$) after interaction with molecular oxygen ($O_2$). Singlet oxygen is the key agent responsible for cellular and tissue damage in PDT, causing oxidation of the target tissue (T); there also is evidence that superoxide ion may be involved.

In 1978, it was reported that a combination of hematoporphyrin derivative (HpD) and light was effective in causing partial or complete tumor necrosis in 111 of 113 tumors in 25 patients. PDT with Photofrin®, a purified HpD, has been approved in Canada for bladder and esophageal cancer; in the Netherlands and France for early and advanced stage esophageal cancer; in Japan for early stage lung, esophageal, gastric, and cervical cancer; and in the United States for advanced stage esophageal and lung cancers. More than 10,000 patients worldwide have been treated with PDT for a multiplicity of tumors accessible to light, including skin, lung, bladder, head and neck, breast, and esophageal cancers. PDT exerts its antitumor effect by several mechanisms, e.g. direct toxicity to tumor cells, occlusion and dissolution of tumor vasculature and microvasculature. In spite of these modes of operation, a number of PDT treated tumors are not cured. Further PDT has little or no effect upon metastatic lesions not exposed to light. In addition, known photodynamic compounds are often ineffective against hypoxic tumor cells and do little to enhance immune response of the organism to undesired hyperproliferative tissue. Therefore, photodynamic therapy, while effective, is not as effective as desired and a method for improving overall efficacy is needed.

Chemotherapy is used a) as adjuvant treatment before and after local treatment for primary disease, with the aim of eradicating occult metastasis and b) in combination with other modalities, including other chemotherapeutic drugs, in an attempt to improve their therapeutic effects. This synergy does not lead to therapeutic benefit unless the interaction between the effects is tumor specific. There has been a recent interest in using biological response modifiers (BRM) as single or adjuvant therapies against cancer. BRMs consist of a large number of molecules that may act to regulate various components of the immune response or other defense mechanisms.

The development of agents that can stimulate or augment the host's immune response against malignancies represents an attractive approach to cancer therapy. Flavone-8-acetic acid (FIG. 1a) is a synthetic flavonoid widely studied in the mid-1980s through 1990s as an agent to treat solid tumors. FAA exerts its antitumor activity, at least in part, by interrupting tumor vascular supply. For example various investigators, using dye perfusion, NMR, RbCl-uptake and Xe-clearance techniques, have shown that FAA causes reduction in tumor blood flow. Little or no alteration in normal tissue blood flow has been observed. While FAA shows in vitro activity against a number of tumor cell lines, in vivo effects, primarily hemorrhagic tumor necrosis are similar to those described following treatment with TNF. FAA induces natural killer cell activity in spleen and other tissues. A comparison of in vitro and in vivo studies using the Lewis lung carcinoma strongly suggested an indirect mode of antitumor action. Mahadevan et al. demonstrated that pretreatment of mice with antiserum to TNF-α could almost completely abrogate the reduction in Colon 26 tumor blood flow induced by FAA. In the same study, FAA was shown to induce in vitro splenocytes and peritoneal exudate cells to produce and release material with TNF-α-like activity (as determined in a functional assay using TNF-sensitive WEHI 164 cells). These observations suggest that the activity of FAA can be attributed to its ability to induce TNF-α in tumors.

In spite of the impressive preclinical activity of FAA, clinical trials have been disappointing due to lack of potency and dose limiting toxicity. Structure-activity studies of analogs of FAA were undertaken to find compounds with similar biological profiles but with increased clinical effectiveness. In the earliest study the topologically related mono-substituted fused-ring analog Xanthenone-4-acetic acid (XAA) proved more efficient than FAA in eliminating Colon 38 tumors. Subsequently, a study by the same group showed that some di-substituted derivatives of XAA, in particular 5,6-Dimethylxanthenone-4-acetic acid (DMXAA; FIG. 1b), had considerably greater dose potencies than FAA against implanted murine tumors. Like FAA, DMXAA has been shown to induce TNF-α along with IFN-γ. The TNF-α is produced almost entirely within the tumor by both tumor cells and tumor-infiltrated host cells. Circulating TNF is markedly lower than that obtained by injecting therapeutic levels of TNF-α or by endogenous induction of TNF-α by LPS administration. This results in a selective tumor response with moderate systemic toxicity. DMXAA, in contrast to FAA, is active in vitro against cultured human and murine cells. It has been shown that exogenous rHuTNF-α potentiates PDT without a concomitant increase in either local or systemic toxicity.

It is therefore an object of the invention to improve effectiveness of photodynamic compounds against hyperproliferative tissue including hypoxic tumor cells, to enhance immune response of the organism to undesired hyperproliferative tissue and to provide effectiveness even in the absence of exposure to light.

BRIEF SUMMARY OF THE INVENTION

In accordance with the invention a novel method is provided for treating undesired hyperproliferative tissue in a mammal. The method includes the steps of: injecting the mammal with a photodynamic compound having a selective uptake in the hyperproliferative tissue and which is activated at a particular light frequency; injecting the mammal with a xanthenone-4-acetic acid or a Group I metal, Group II metal or quaternary salt thereof near the time of maximum uptake of the photodynamic compound in the hyperproliferative tissue; and exposing the hyperproliferative tissue to light at the particular frequency that activates the photodynamic compound.

The method of the invention causes necrosis of the hyperproliferative tissue to an extent greater than can be obtained by either the photodynamic compound or xanthenone-4-acetic acid alone. Further and surprisingly the method enhances immune response of the mammal to the hyperproliferative tissue even after the photodynamic compound and xanthenone-4-acetic acid are no longer present in the mammal.

DETAILED DESCRIPTION OF THE INVENTION

Figure 1A:
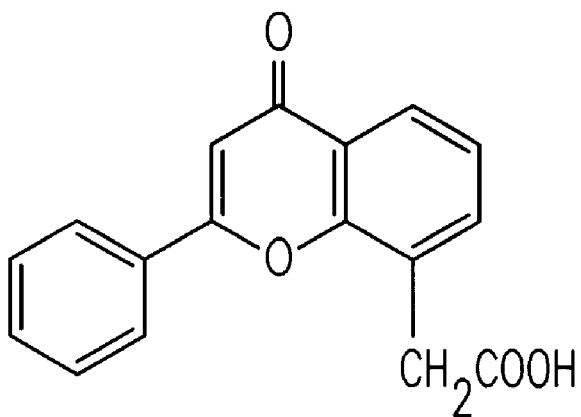
FIG. 1A shows the chemical structure of FAA.
Figure 1B:
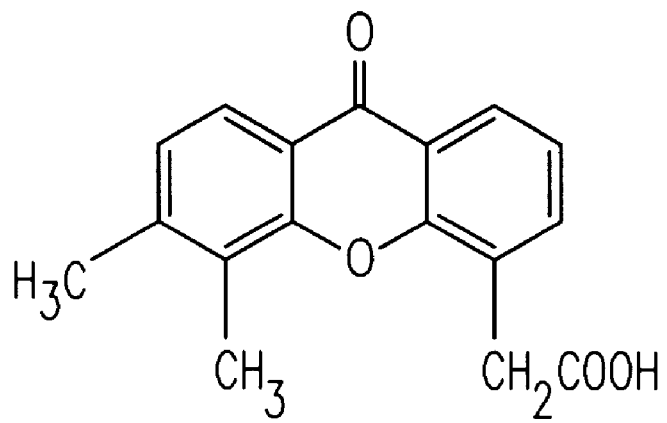
FIG. 1B shows the chemical structure of DMXAA.

The hyperproliferative tissue subject to treatment in accordance with the method of the invention is any tissue that grows uncontrollably in the mammal such as tumors and hyperproliferative blood vessels as may be found in AMD. The method is especially suitable for both large and small tumors that may be metastatic. The tumors may me micro tumors or may be hypoxic.

The method is applicable to essentially any mammal since the operation of photodynamic compound is mammal independent. Further, since the xanthanone-4-acetic acid (XAA) induces tumor necrosis factor (TNF) by the same mechanism regardless of the mammal involved, the use of XAA is also mammal independent. The method is therefore applicable to all mammals, especially rodents and primates.

The photodynamic compound is usually any porphyrin related compound, e.g. porfimer sodium sold under the trademark PHOTOFRIN®, and derivatives of chlorin and bacteriochlorin as for example described in U.S. Pat. Nos. 4,866,168; 5,002,962; 5,028,621; 5,093,349; 5,173,504; 5,190,966; 5,198,460; 5,225,433; 5,314,905; 5,459,159; 5,498,710; 5,591,847; 5,864,035 and 6,103,751. The photodynamic compound is usually employed in an amount of about 1 to about 10 mg/kg of body weight of the mammal. When the photodynamic compound is porfimer sodium, the light frequency used is about 630 nm at an energy of about 100 to about 225 $J/cm^2$.

The xanthenone-4-acetic acid is xanthenone-4-acetic acid and its substituted derivatives, especially dialkylxanthenone-4-acetic acid and preferably 5,6-dialkylxanthenone-4-acetic acid. The dialkylxanthenone acetic acid is most commonly dimethylxanthenone acetic acid (DMXAA) used in a concentration of about 10 to about 30 mg/kg of body weight of the mammal. It is to be understood that the term xanthanone-4-acetic acid includes its substituted derivatives, especially its alkyl substituted derivatives and is intended to include its Group I and Group II metal and ammonium and quaternary salts.

DMXAA in principle can be successfully combined with PDT for the following reasons: a) the differing systemic toxicities of these two modalities allow for their combination, at close to full tolerated doses, with additive effects against tumors and less than additive toxicities to normal tissues, b) published results suggest that DMXAA is more effective against hypoxic tumor cells, precisely those cells that are most likely to be resistant to PDT, and c) the BRM properties of DMXAA in combination with PDT can stimulate immunity against the tumor. Our preliminary data with the syngeneic murine fibrosarcoma RIF-1 suggests that PDT with adjuvant DMXAA results in both increased antitumor activity without concomitant toxicity and immunogenicity against the tumor. Optimization of this latter property can result in the successful eradication of occult micrometastases.

The method of the invention is a method or process to locally treat malignant tumors by combining photodynamic therapy with a substance capable of modifying a biological response, and is a method or process to stimulate tumor immunity resulting in the control of primary tumors and occult metastases by combining photodynamic therapy with a substance capable of modifying a biological response.

PDT and DMXAA or related biological response modifying compounds are applied using doses and intervals between the application of each therapy so that a strong, immediate antitumor response is obtained.

PDT and DMXAA or related biological response modifying compounds are applied using doses and intervals between the application of each modality so that a delayed antitumor response is obtained. The delayed response may require a weak and ineffective immediate antitumor response. The delayed response unexpectedly leads to the immunity of the subject to subsequent tumor growth.

Figure 2A:
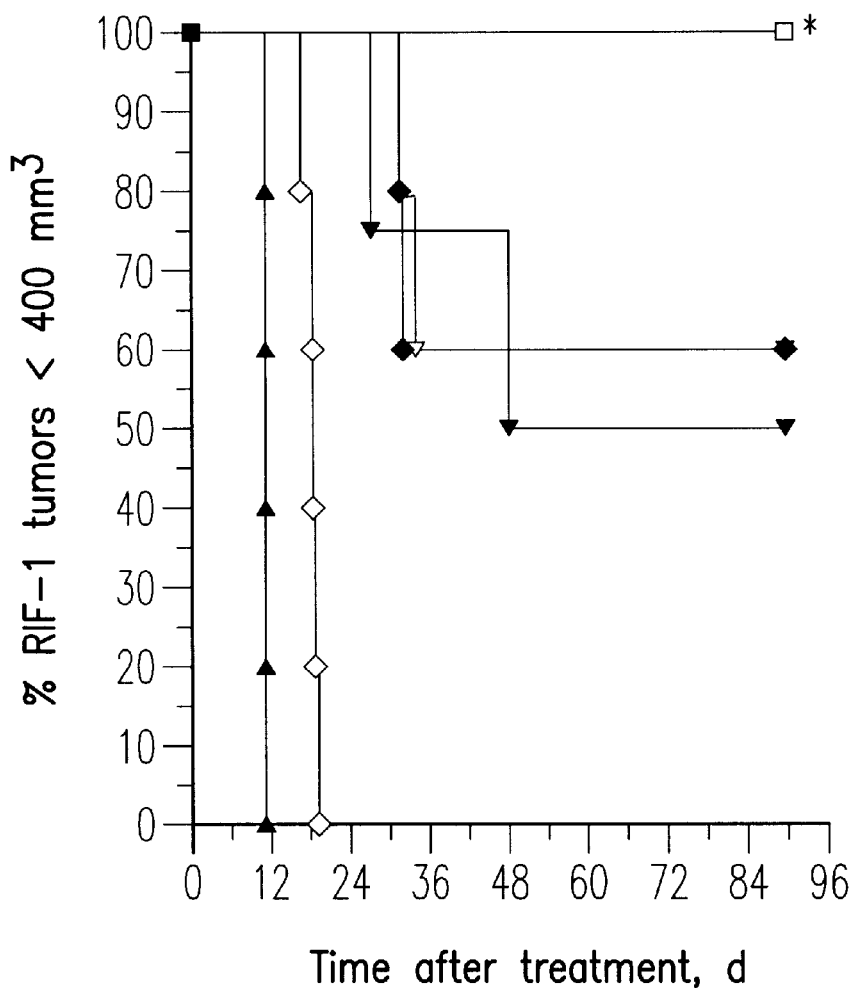
FIG. 2A is a graph showing dose response of RIF-1 tumors to PDT using porfimer sodium (Photofrin®) using 630 nm laser light at varying doses and light energies.
Figure 2A:
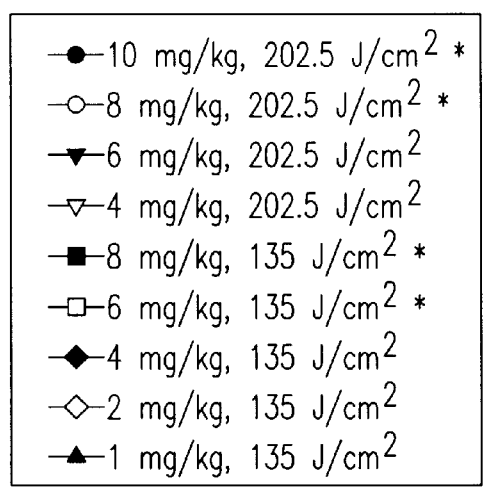
Figure 2B:
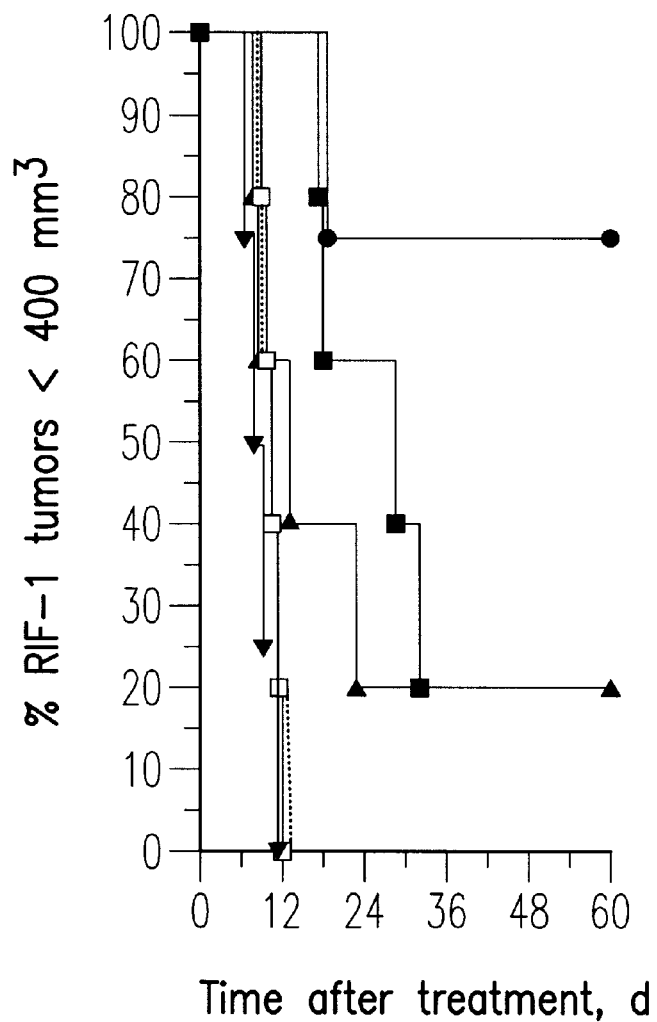
FIG. 2B is a graph showing dose response of RIF-1 tumors to DMXAA at varying doses.
Figure 2B:
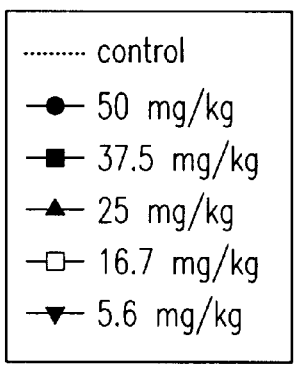

The drawings illustrate the responses of RIF-1 tumors to either PDT (FIG. 2a) or DMXAA (FIG. 2b). Dose response data are shown in the form of Kaplan-Meier 'survival' plots, where the percent of RIF-1 tumors with volumes less than 400 mm are plotted against time from treatment. Tumor volumes at the time of treatment were 50–70 mg (approximately 3% of the mouse body mass). Both PDT and DMXAA, when administered alone, can control tumors in a dose-dependent manner. However, the most effective doses are at or near the treatment toxic limits in this mouse model. It is thought that morbidity and mortality following large PDT doses are at least in part model specific; i.e., local treatment of the tumor results in the illumination of a relatively sizable volume of the subject vis-a-vis much larger subjects like human patients.

Figure 3:
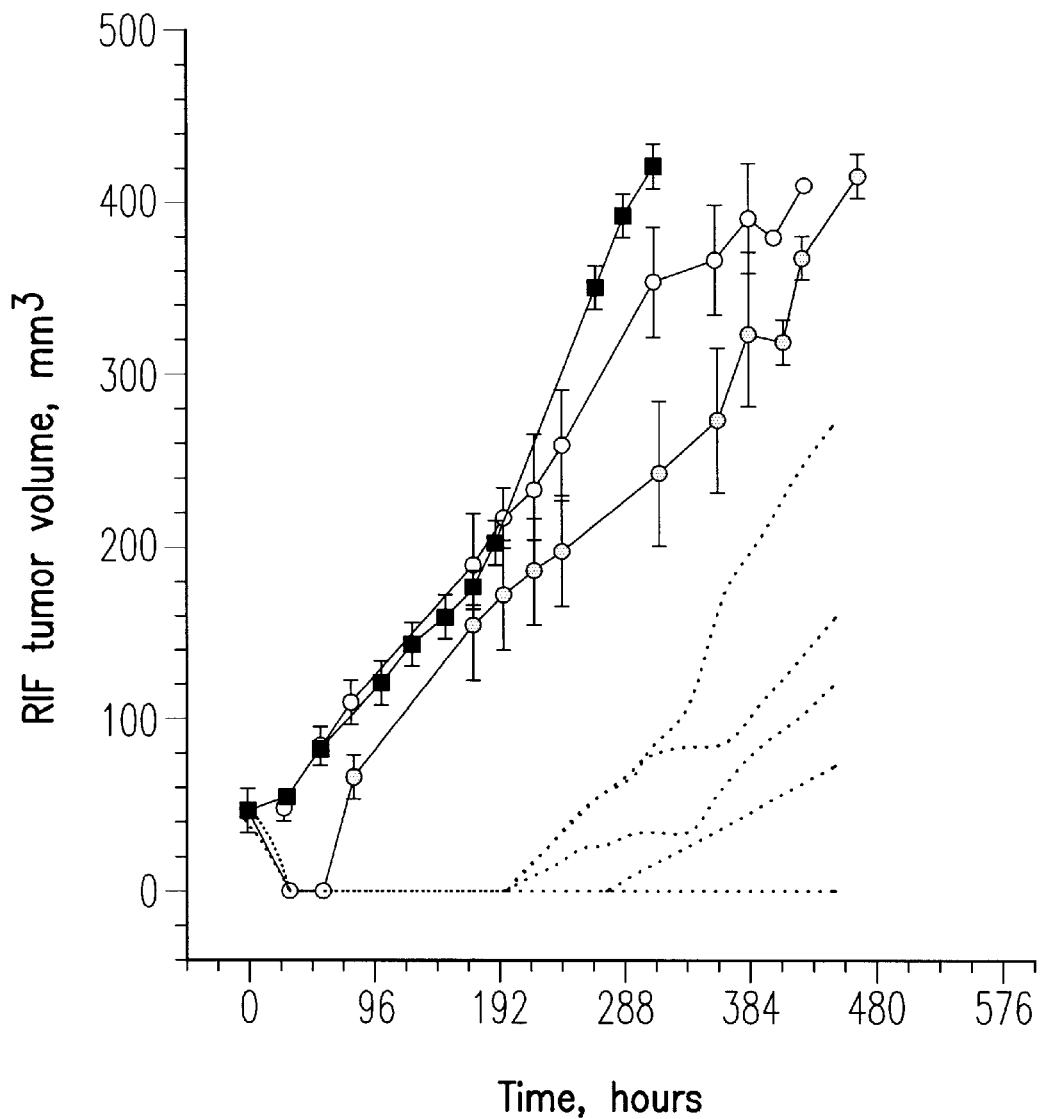
FIG. 3 is a graph showing response of RIF-1 tumors to PDT+DMXAA.

In pilot studies of PDT plus adjuvant DMXAA only low doses of each modality were chosen. FIG. 3 shows RIF-1 tumor regrowth using the following conditions: 2 mg Photofrin/kg. 23 hours, 20 mg DMXAA/kg. 2 hours, 135 J/cm$^2$ 63-nm laser light. Control tumors (no drug, no light) are shown as solid black squares; DMXAA are shown as open circles; PDT alone as gray circles. When PDT and DMXAA were combined (individual tumors are shown as dotted lines) there was a 10 day delay in tumor regrowth, with 1/5 tumors controlled past 60 days.

Figure 4:
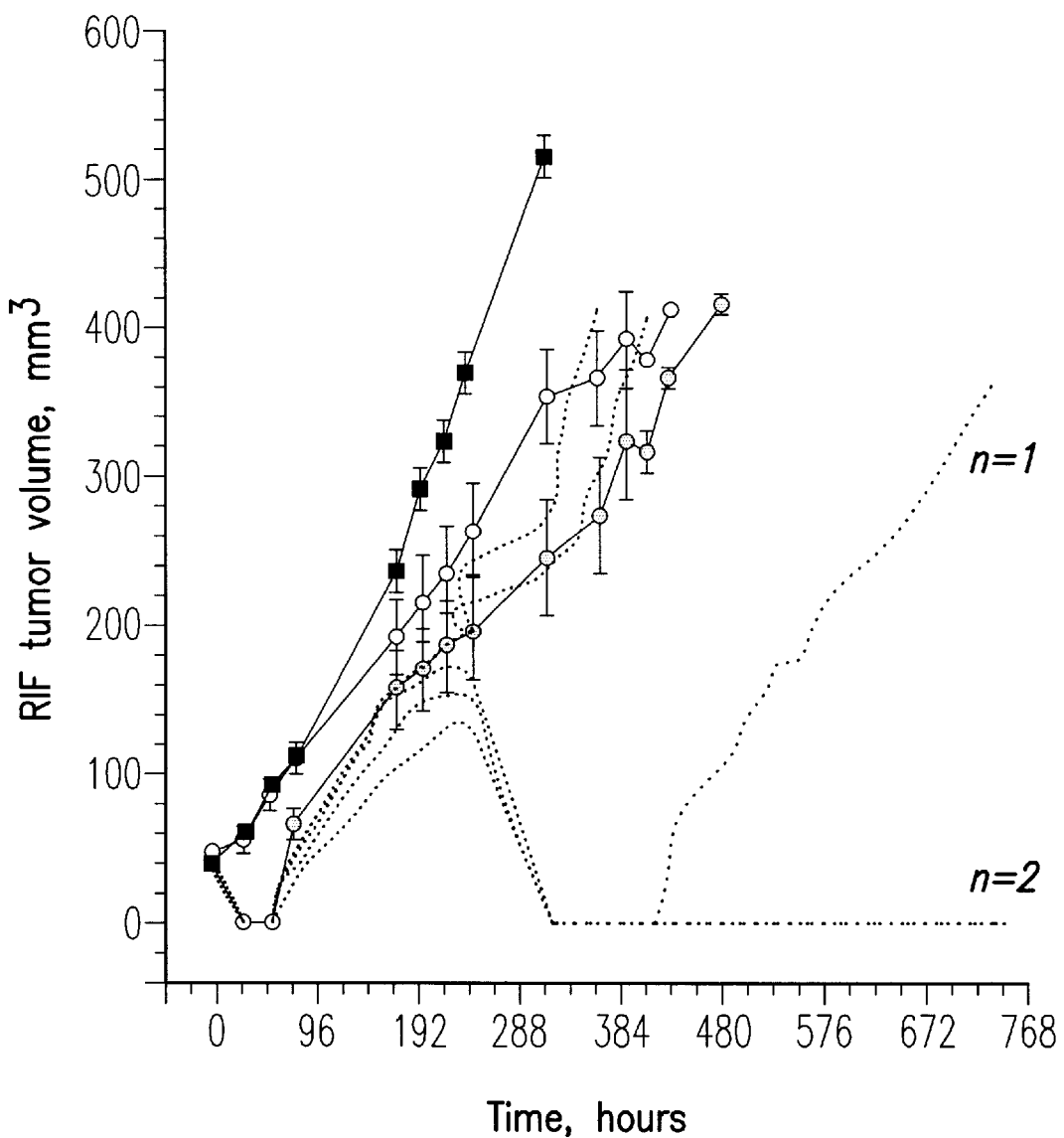
FIG. 4 is a graph showing response of RIF-1 tumors to PDT+DMXAA showing a weak immediate response followed by a delayed tumor response.

FIG. 4 shows tumor response using slightly different conditions: 2 mg Photofrin/kg, 23 hours, 20 mg DMXAA/kg, 1 hour, 135 J/cm$^2$ $^{630}$-nm laser light. The symbols in the graph are the same as for FIG. 3. All five mice in the combined treatment group had weak immediate responses, i.e., only a two-day regrowth delay. However, 3 of 5 tumors had a delayed response, where tumor volumes decreased over two days time from ~160 mm$^3$ to zero volume; 1 of 3 tumors undergoing this late response regrew after a 4 day delay. This delayed response has been observed using other treatment conditions where the initial response was considered weak (data not shown). Delayed responses are not obtained following strong immediate tumor responses to combination therapy, nor have delayed responses been seen in any control group.

Figure 5:
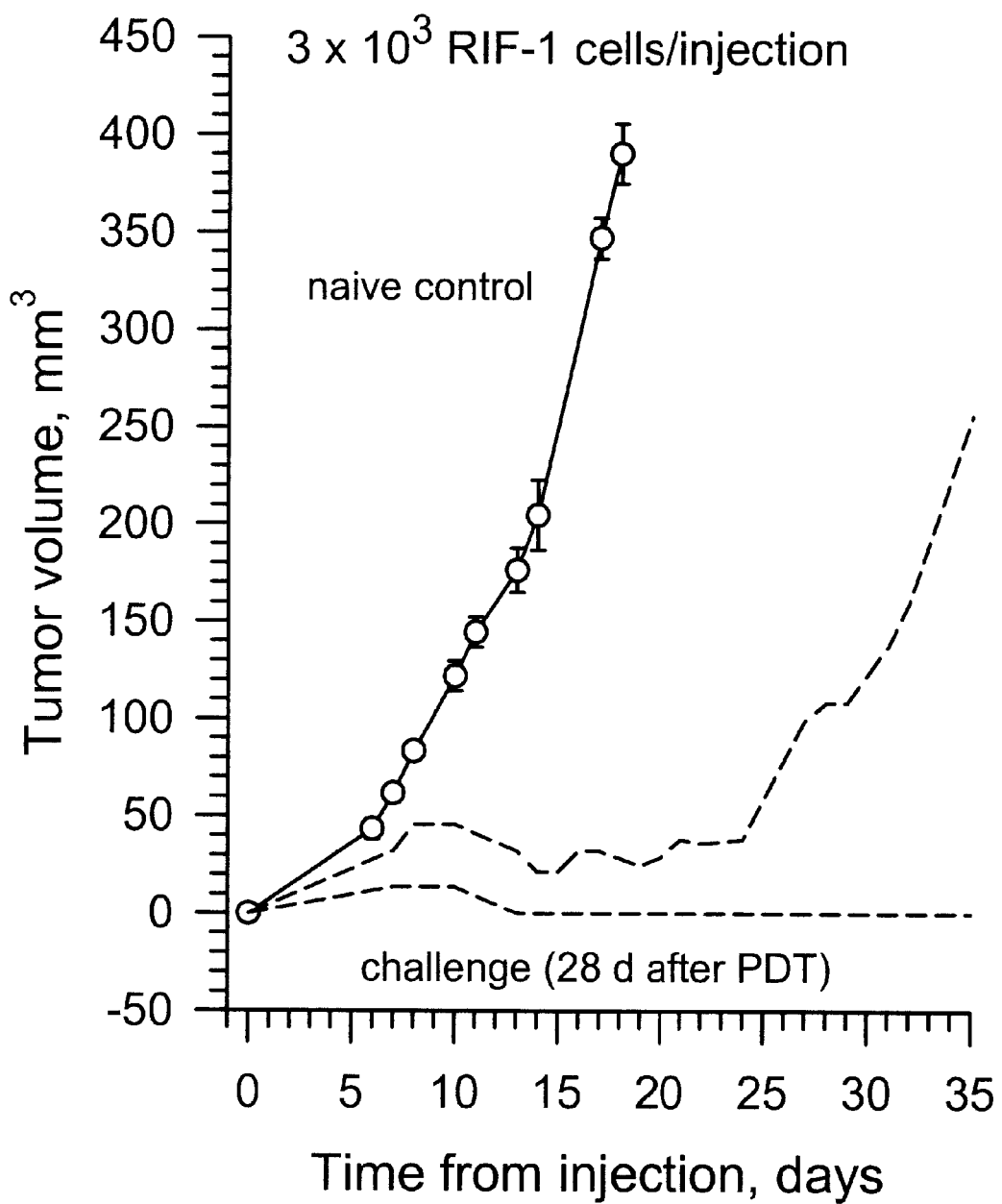
FIG. 5 is a graph showing a challenge of C3H mice with RIF-1 tumors following tumor regression of original tumors treated with a combination of PDT and DMXAA resulting in a delayed response.

One month after treatment the two mice with controlled tumors (shown at the bottom of FIG. 4) were reinjected with a standard tumoring dose of 3×10$^5$ RIF-1 cells (on the shoulder opposite that of the original treated tumor). As seen in FIG. 5, after a small amount of growth, one tumor regressed to zero volume and has remained so for >1 month; the second tumor had some initial growth and remained static for several weeks before regrowing. This response is indicative of an acquired immune response against this tumor line, and as such this therapy can be used to control both primary tumors and occult micrometastatic malignancies.

What is claimed is:

1. A method for treating hyperproliferative tissue in a mammal which comprises:

a) injecting the mammal containing a tumor with a photodynamic compound having tumor selective uptake which is activated at a particular light frequency;

b) injecting the mammal with a xanthenone-4-acetic acid or group I metal, Group II metal, ammonium or quaternary salt thereof, proximate the time of maximum tumor uptake of the photodynamic compound; and c) exposing the tumor to light at the particular frequency that activates the photodynamic compound.

2. The method of claim 1 where the hyperproliferative tissue is a tumor.

3. The method of claim 2 where the photodynamic compound is porfimer sodium injected at a dose of about 1 to about 10 mg/kg of body weight of the mammal and the light frequency is 630 nm at an energy of about 100 to about 225 J/cm$^2$.

4. The method of claim 3 where the xanthanone-4-acetic acid is 5,6-dialkylxanthanone-4-acetic acid.

5. The method of claim 3 wherein the xanthanone-4-acetic acid is 5,6-dimethylxanthanone-4-acetic acid.

6. The method of claim 5 wherein the 5,6-dimethylxanthanone-4-acetic acid is injected at a dose of about 5 to about 50 mg/kg of body weight of the mammal.

7. The method of claim 6 wherein the 5,6-dimethylxanthanone-4-acetic acid is injected at a dose of about 10 to about 30 mg/kg of body weight of the mammal.

* * * * *

UNITED STATES PATENT AND TRADEMARK OFFICE
CERTIFICATE OF CORRECTION

PATENT NO.    : 6,495,585 B2
DATED         : December 17, 2002
INVENTOR(S)   : Bellnier et al.

It is certified that error appears in the above-identified patent and that said Letters Patent is hereby corrected as shown below:

<u>Title page,</u>
Item [*] Notice, "Subject to any disclaimer, the term of this patent is extended or adjusted under 35 USC 154(b) by (34) days", delete the phrase by "34 days" and insert -- by 0 days --

Signed and Sealed this

Fourteenth Day of October, 2003

JAMES E. ROGAN
*Director of the United States Patent and Trademark Office*